(12) United States Patent
Kang et al.

(10) Patent No.: US 11,786,180 B2
(45) Date of Patent: Oct. 17, 2023

(54) APPARATUS AND METHOD FOR ESTIMATING BIO-INFORMATION

(71) Applicant: SAMSUNG ELECTRONICS CO., LTD., Suwon-si (KR)

(72) Inventors: Jae Min Kang, Seoul (KR); Yong Joo Kwon, Yongin-si (KR); Youn Ho Kim, Hwaseong-si (KR); Sang Yun Park, Hwaseong-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 315 days.

(21) Appl. No.: 16/811,774

(22) Filed: Mar. 6, 2020

(65) Prior Publication Data

US 2021/0022677 A1    Jan. 28, 2021

(30) Foreign Application Priority Data

Jul. 25, 2019    (KR) .......................... 10-2019-0090105

(51) Int. Cl.
*A61B 5/02* (2006.01)
*A61B 5/00* (2006.01)
(Continued)

(52) U.S. Cl.
CPC .......... *A61B 5/6843* (2013.01); *A61B 5/0205* (2013.01); *A61B 5/681* (2013.01);
(Continued)

(58) Field of Classification Search
CPC ........ A61B 2562/0247; A61B 5/02108; A61B 5/6843; A61B 5/0261; A61B 5/442;
(Continued)

(56) References Cited

U.S. PATENT DOCUMENTS

| 9,665,213 B2 | 5/2017 | Christman et al. |
| 2008/0077024 A1 | 3/2008 | Schnall |

(Continued)

FOREIGN PATENT DOCUMENTS

| CN | 104423767 A | 3/2015 |
| EP | 3 603 507 A1 | 2/2020 |

(Continued)

OTHER PUBLICATIONS

Chandrasekhar, Anand et al., "Smartphone-based blood pressure monitoring via the oscillometric finger-pressing method", Science Translational Medicine, vol. 10, eaap8674, Mar. 7, 2018, pp. 1-11. (12 pages total).

(Continued)

*Primary Examiner* — Deborah L Malamud
(74) *Attorney, Agent, or Firm* — Sughrue Mion, PLLC

(57) ABSTRACT

An apparatus for estimating bio-information is provided. The apparatus for estimating bio-information may include: a pulse wave sensor configured to measure a pulse wave signal from an object; a force sensor configured to measure a force exerted by the object to the pulse wave sensor; and a processor configured to obtain a contact pressure based on the force and a reference contact area between the object and a contact surface, and estimate bio-information based on the contact pressure and the pulse wave signal.

17 Claims, 19 Drawing Sheets

(51) Int. Cl.
  *A61B 5/0205*  (2006.01)
  *G01L 5/00*  (2006.01)
  *A61B 5/021*  (2006.01)
  *A61B 5/024*  (2006.01)
  *A61B 5/16*  (2006.01)

(52) U.S. Cl.
  CPC ............ *A61B 5/6898* (2013.01); *A61B 5/742* (2013.01); *A61B 5/7485* (2013.01); *G01L 5/0038* (2013.01); *A61B 5/02007* (2013.01); *A61B 5/02108* (2013.01); *A61B 5/02427* (2013.01); *A61B 5/165* (2013.01); *A61B 2560/0223* (2013.01)

(58) Field of Classification Search
  CPC ... A61B 5/681; A61B 5/02427; A61B 5/7264; A61B 5/00; A61B 5/0004; A61B 5/7275; A61B 2562/06; A61B 5/0059; A61B 5/0082; A61B 5/02; G16H 50/20
  See application file for complete search history.

(56) References Cited

U.S. PATENT DOCUMENTS

| | | |
|---|---|---|
| 2009/0143655 A1 | 6/2009 | Shani |
| 2010/0168531 A1 | 7/2010 | Shaltis et al. |
| 2015/0062078 A1 | 3/2015 | Christman et al. |
| 2015/0335293 A1 | 11/2015 | Christman et al. |
| 2016/0058375 A1* | 3/2016 | Rothkopf ............... G04B 39/02 600/323 |
| 2017/0251935 A1 | 9/2017 | Yuen |
| 2018/0110427 A1 | 4/2018 | Kang et al. |
| 2018/0177413 A1 | 6/2018 | Kwon et al. |
| 2018/0235489 A1 | 8/2018 | Mouradian et al. |
| 2020/0037956 A1 | 2/2020 | Kang et al. |

FOREIGN PATENT DOCUMENTS

| | | |
|---|---|---|
| JP | 2006-239114 A | 9/2006 |
| KR | 10-2006-0081178 A | 7/2006 |
| KR | 10-2018-0076050 A | 7/2018 |
| WO | 2017/152098 A1 | 9/2017 |
| WO | 2018/081314 A1 | 5/2018 |

OTHER PUBLICATIONS

Chandrasekhar, Anand et al., "An iPhone Application for Blood Pressure Monitoring via the Oscillometric Finger Pressing Method", Scientific Reports, vol. 8, No. 13136, 2018, pp. 1-6. (6 pages total).
Communication dated Nov. 20, 2020 issued by the European Patent Office in European Patent Application No. 20174963.7.
Communication dated Jul. 30, 2023 by the National Intellectual Property Administration of P.R. China in Chinese Patent Application No. 202010252845.5.

* cited by examiner

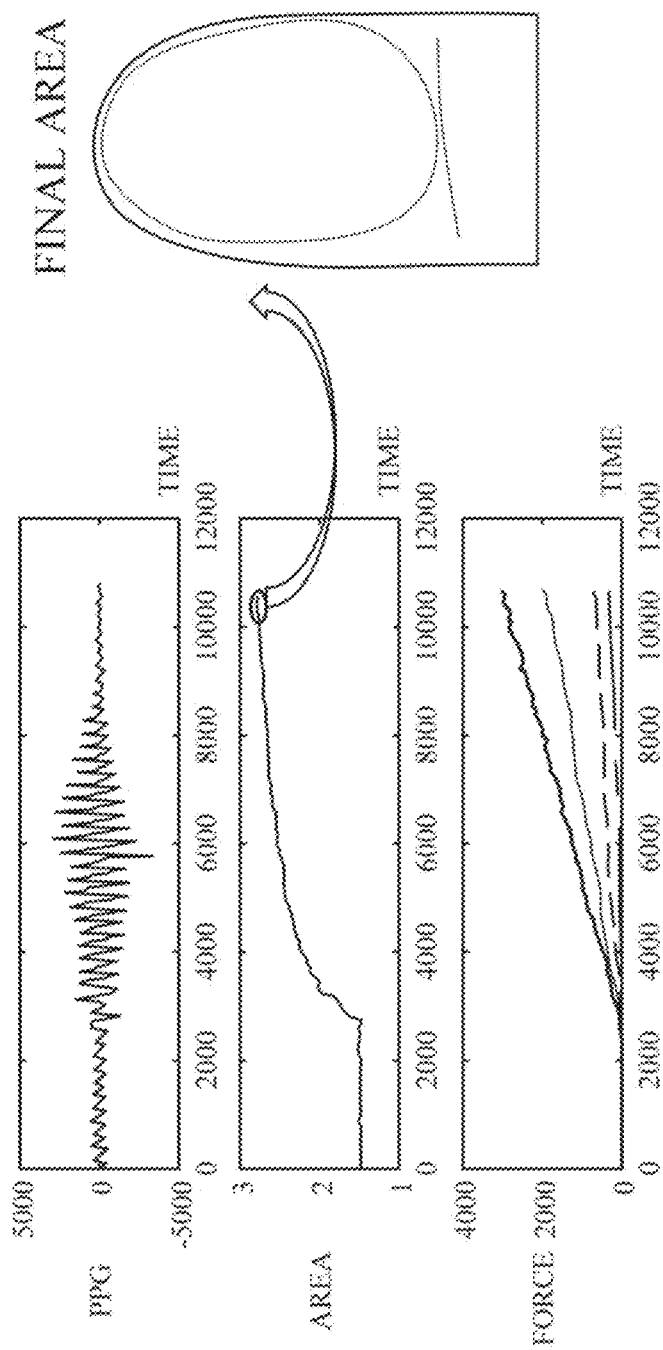

APPARATUS AND METHOD FOR ESTIMATING BIO-INFORMATION

CROSS-REFERENCE TO RELATED APPLICATION

This application claims priority from Korean Patent Application No. 10-2019-0090105, filed on Jul. 25, 2019, in the Korean Intellectual Property Office, the disclosure of which is incorporated herein by reference in its entirety.

BACKGROUND

1. Field

Example embodiments of the disclosure relate to estimating bio-information, and more particularly to cufflessly estimating blood pressure.

2. Description of Related Art

Generally, methods of non-invasively measuring blood pressure may include a method of measuring a cuff-based pressure and a method of estimating blood pressure by measuring pulse waves without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

According to an aspect of an example embodiment, there is provided an apparatus for estimating bio-information, including: a pulse wave sensor configured to measure a pulse wave signal from an object; a force sensor configured to measure a force exerted by the object to the pulse wave sensor; and a processor configured to obtain a contact pressure based on the force and a reference contact area between the object and a contact surface, and estimate bio-information based on the contact pressure and the pulse wave signal.

The pulse wave sensor may include: a light source configured to emit a light onto the object; and a detector configured to detect the light reflected or scattered from the object.

The apparatus may further include a storage configured to store the reference contact area, wherein when the pulse wave signal is measured, the processor may be further configured to retrieve the reference contact area from the storage.

The processor may be further configured to determine whether to perform calibration on the reference contact area, and in response to determining to perform the calibration, obtain the reference contact area and update the reference contact area in the storage.

The processor may be further configured to determine whether to perform the calibration based on at least one of a determination of whether the storage stores the reference contact area, a user's request, a predetermined calibration interval, and bio-information estimation history.

The processor may be further configured to obtain the reference contact area by receiving an input of the reference contact area from a user or from an external device, or by using at least one of a display and an image sensor included in the apparatus for estimating bio-information.

The processor may be further configured to obtain the reference contact area based on a residual fingerprint image which remains on the display after the user contacts the display with the object.

The processor may be further configured to execute an area measurement application to measure a size of the residual fingerprint image, and obtain the size of the residual fingerprint image as the reference contact area.

The display may include a touch screen; and when the user contacts the display with the object, the processor may be further configured to obtain the reference contact area based on touch data generated from the touch screen.

The processor may be further configured to calculate a statistics value of pixel intensities of the touch data, and obtain the reference contact area by inputting the statistics value to an area conversion function.

The display may include a fingerprint sensor that provides the contact surface which has a larger surface area than a surface area of the pulse wave sensor, and disposed separately from the pulse wave sensor.

By using an image sensor, the processor may be further configured to acquire an image of the object when the object comes into contact with an external object, or a fingerprint image which remains after the object comes into contact with the external object and then moves apart from the external object, and obtain the reference contact area based on the image of the object or the fingerprint image of the object.

The processor may be further configured to obtain an oscillometric envelope which represents an amplitude of the pulse wave signal versus the contact pressure, and estimate the bio-information based on the oscillometric envelope.

Upon receiving a request for estimating the bio-information, the processor may be further configured to provide information indicating at least one of a contact position of the object and a contact force to be exerted by the object to the pulse wave sensor.

The bio-information may include one or more of blood pressure, vascular age, arterial stiffness, aortic pressure waveform, vascular compliance, stress index, and degree of fatigue.

According to an aspect of another example embodiment, there is provided a method of estimating bio-information, including: measuring a pulse wave signal from an object; measuring a force exerted by the object; obtaining a contact pressure based on the force and a reference contact area between the object and a contact surface; and estimating bio-information based on the contact pressure and the pulse wave signal.

The method may further include, in response to determining that no reference contact area is stored for the object, or in response to determining that a calibration of the reference contact area is required, performing the calibration for obtaining the reference contact area.

The performing the calibration may include obtaining the reference contact area by receiving an input of the reference contact area from a user or from an external device, or by using at least one of a display and an image sensor included in an apparatus for performing the estimating of the bio-information.

The performing the calibration may include obtaining the reference contact area based on a residual fingerprint image which remains on the display after a user contacts the display with the object.

The performing the calibration may include: executing an area measurement application to measure a size of the residual fingerprint image; and obtaining the size of the residual fingerprint image as the reference contact area.

The performing the calibration may include, when the user contacts the display with the object, obtaining the reference contact area based on touch data generated from a touch screen of the display.

The performing the calibration may include: calculating a statistics value of pixel intensities of the touch data; and obtaining the reference contact area by inputting the statistics value to an area conversion function.

The performing the calibration may include, when the user contacts the display with the object, obtaining the reference contact area based on fingerprint data generated by a fingerprint sensor of the display.

The performing the calibration may include: by using the image sensor, acquiring an image of the object when the object comes into contact with an external object, or a fingerprint image which remains after the object comes into contact with the external object and then moves apart from the external object; and obtaining the reference contact area based on the image of the object or the fingerprint image of the object.

The estimating the bio-information may include obtaining an oscillometric envelope which represents an amplitude of the pulse wave signal versus the contact pressure, and estimating the bio-information based on the oscillometric envelope.

BRIEF DESCRIPTION OF THE DRAWINGS

The above and/or other aspects will be more apparent by describing certain example embodiments, with reference to the accompanying drawings, in which:

FIGS. 4A and 4B are diagrams explaining a relationship between a change in contact pressure of an object and a contact area;

DETAILED DESCRIPTION

Figure 1:
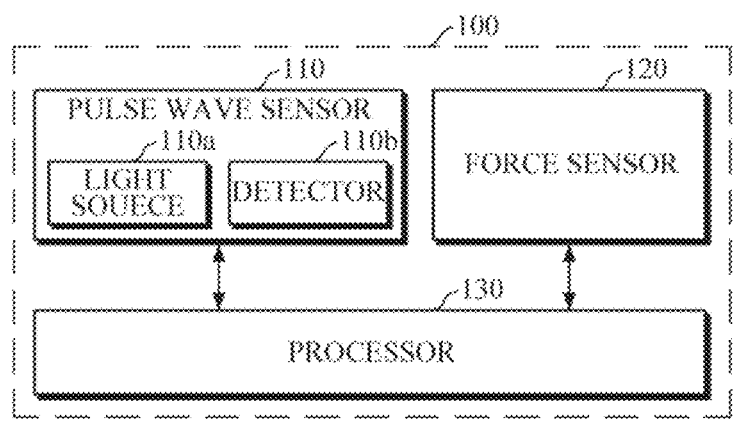
FIGS. 1 and 2 are block diagram illustrating an apparatus for estimating bio-information according to example embodiments of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations, such as "comprise" or "comprising", will be understood to imply the inclusion of stated elements but not the exclusion of any other elements. Terms, such as 'part' and 'module' denote units that process at least one function or operation and they may be implemented by using hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of an apparatus and method for estimating bio-information will be described in detail with reference to the accompanying drawings.

Figure 2:
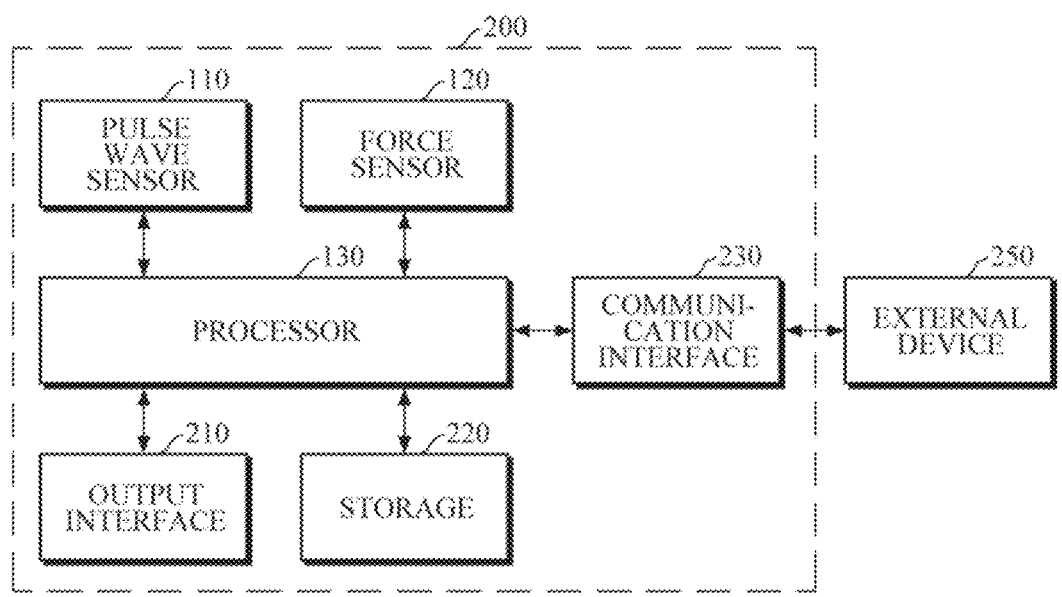

FIGS. 1 and 2 are block diagram illustrating an apparatus for estimating bio-information according to example embodiments of the present disclosure.

Apparatuses 100 and 200 for estimating bio-information according to example embodiments of the present disclosure may be embedded in a medical device used in a specialized medical institution, a smartwatch worn on a wrist, various types of wearable devices such as a smart band type wearable device, a headphone type wearable device, a headband type wearable device, and the like, or a mobile device such as a smartphone, a tablet personal computer (PC), and the like, but are not limited thereto.

Referring to FIGS. 1 and 2, the apparatuses 100 and 200 for estimating bio-information include a pulse wave sensor 110, a force sensor 120, and a processor 130. The pulse wave sensor 110 may measure a pulse wave signal, including a photoplethysmography (PPG) signal, from an object. The pulse wave sensor 110 may include a light source 110a which emits light onto the object to detect an optical signal from the object; and a detector 110b which detects scattered or reflected light when light emitted by the light source 110a is scattered or reflected from body tissue of the object such as a skin surface or blood vessels. The light source 110a may include a light emitting diode (LED), a laser diode (LD), a phosphor, and the like, but is not limited thereto. The detector 110b may include a photo diode, a photo transistor (PTr), an image sensor (e.g., complementary metal-oxide-semiconductor (CMOS) image sensor), and the like, but is not limited thereto. The pulse wave sensor 110 may be formed in various structures, such as a structure having a plurality of light sources 110a and one detector 110b, a structure having an array of pairs of light sources 110a and detectors 110b, and the like, without any specific limitations.

When a user gradually increases force applied to the pulse wave sensor 110 while contacting an object with the pulse wave sensor 110 to estimate bio-information, or when a user gradually decreases force after applying a force greater than or equal to a threshold, the force sensor 120 may measure the contact force.

The processor 130 may process various operations related to estimating bio-information. For example, upon receiving a request for estimating bio-information from a user, or if predetermined criteria for estimating bio-information are satisfied, the processor 130 may control the pulse wave sensor 110 and the force sensor 120. The processor 120 may be electrically connected to the pulse wave sensor 110 and the force sensor 120, and may receive the pulse wave signal and the contact force from the pulse wave sensor 110 and the force sensor 120, respectively.

The processor 130 may estimate bio-information based on the received pulse wave signal and contact force. The bio-information may include heart rate, blood pressure, vascular age, arterial stiffness, aortic pressure waveform, vascular compliance, stress index, degree of fatigue, skin elasticity, skin age, and the like, but is not limited thereto. Hereinafter, a description will be given, if necessary, using blood pressure as an example for convenience of explanation.

Upon receiving the contact force, the processor 130 may obtain contact pressure based on the received contact force and a reference contact area. For example, the processor 130 may obtain a contact pressure value by dividing the contact force by the reference contact area. The reference contact area may be a value pre-obtained for each object by calibration before a current estimation time of bio-information, and may be a value corresponding to a contact area at a final time (e.g., a contact pressure measurement time) when a pressure exerted from the object onto the apparatus 100 reaches a predetermined pressure (or a predetermined maximum pressure) while the object is in contact with the pulse wave sensor 110. The reference contact area may be obtained for various objects, such as an index finger of the right hand, an index finger of the left hand, an upper portion of the wrist, and the like. For example, the apparatus 100 may request the user to contact the apparatus 100 with his/her finger, and may measure and store a contact area between the apparatus 100 and the finger, before the processor 130 obtains the contact pressure, or while the processor 130 is measuring the contact pressure.

For example, the reference contact area at the final time, which is obtained as the object contacts and applies pressure, may be obtained by using a display module or an image sensor, which is mounted at the apparatus 100 for estimating bio-information or an external device, or other hard and flat object. However, the reference contact area is not necessarily limited to the contact area at the final time when the maximum pressure is applied, and may be obtained according to various criteria, for example, a contact area at a time when a predetermined force is applied, a statistics value of contact areas at a plurality of times, and the like. Further, the reference contact area may be calibrated again if predetermined criteria are satisfied.

In addition, the processor 130 may estimate bio-information based on the obtained contact pressure and the measured pulse wave signal. For example, the processor 130 may obtain features related to blood pressure based on the pulse wave signal and the contact pressure, and may estimate blood pressure based on the obtained features. The processor 130 may obtain an oscillometric envelope, which represents an amplitude of the pulse wave signal versus the contact pressure, based on the pulse wave signal and the contact pressure, and may obtain features by using the oscillometric envelope.

Further, upon receiving a request for estimating bio-information, the processor 130 may generate guide information on a contact position between the object and the pulse wave sensor 110 and/or a contact force to be applied by the object to the pulse wave sensor 110, for measuring a pulse wave signal. For example, in order to induce a change in amplitude of the pulse wave signal, the guide information may include information for inducing a gradual increase in contact force while an object is in contact with the pulse wave sensor 110. The guide information may include information for inducing a gradual decrease in contact force when a contact force greater than or equal to a predetermined threshold value is applied. In addition, upon obtaining a contact force actually applied by the object to the pulse wave sensor 110, the processor 130 may determine a contact state based on the obtained contact force and may generate guide information based on the determined contact state.

Referring to FIG. 2, the apparatus 200 for estimating bio-information may further include an output interface 210, a storage 220, and a communication interface 230.

The output interface 210 may output the pulse wave signal and the contact force, obtained by the pulse wave sensor 110 and the force sensor 120 respectively, and/or various processing results of the processor 130, under the control of the processor 130. For example, the output interface 210 may visually output an estimated bio-information value and/or guide information through a display module, or may non-visually output the information by voice, vibrations, tactile sensation, and the like using a speaker module, a haptic module, and the like. A display area may be divided into two or more areas, in which the output interface 210 may output a pulse wave signal, a contact force, and/or contact pressure, which are used for estimating bio-information, in the form of various graphs in a first area. Along with the information, the output interface 210 may output an estimated bio-information value in a second area. If the estimated bio-information value falls outside a normal range, the output interface 210 may output warning information in various manners, such as highlighting an abnormal value in red and the like, displaying the abnormal value along with a normal range, outputting a voice warning message, adjusting a vibration intensity, and the like.

The storage 220 may store the pulse wave signal and the contact force, obtained by the pulse wave sensor 110 and the force sensor 120 respectively, and/or various processing results of the processor 130, under the control of the processor 130. Further, the storage 220 may store a variety of reference information required for estimating bio-information. For example, the reference information may include user characteristic information such as a user's age, sex, health condition, and the like. In addition, the reference information may include a variety of information such as a bio-information estimation model, criteria for estimating bio-information, a reference contact area of each object, and the like, but is not limited thereto.

The storage 220 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Once the pulse wave signal and the contact force are measured, the processor 130 may refer to the storage 220 to extract a reference contact area for an object of a user which is in contact, and may obtain contact pressure by using the extracted reference contact area. The processor 130 may determine whether it is required to calibrate the reference contact area stored in the storage 220. For example, the processor 130 may determine that a calibration of the reference contact area is required when the reference contact area is not stored in the storage 220, when the reference contact area is stored in the storage 220 and is used for estimating bio information for the first time, when the apparatus 100 or 200 is initialized or reset, and/or when there is a change in the object between a first point in time when the reference contact area is measured and stored in the storage 220 and a second point in time when the reference contact area is retrieved from the storage 220 to obtain the contact pressure. Upon determining that calibration is required, the processor 130 may obtain again a reference contact area for the object of the user, and may update the reference contact area of the storage 220 by using the obtained reference contact area.

The communication interface 230 may communicate with an external device 250 by using wired or wireless communication techniques under the control of the processor 130, and may transmit and receive various data to and from the external device 250. For example, the communication interface 230 may transmit a bio-information estimation result to the external device 250, and may receive, from the external device 250, a variety of reference information required for estimating bio-information. For example, the communication interface 230 may transmit a request for a reference contact area to the external device 250. Once the external device 250 receives a reference contact area from the object of the user, the communication interface 230 may receive the reference contact area from the external device 250. The external device 250 may include a cuff-type blood pressure measuring device and an information processing device such as a smartphone, a tablet PC, a desktop computer, a laptop computer, and the like.

Examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 3:
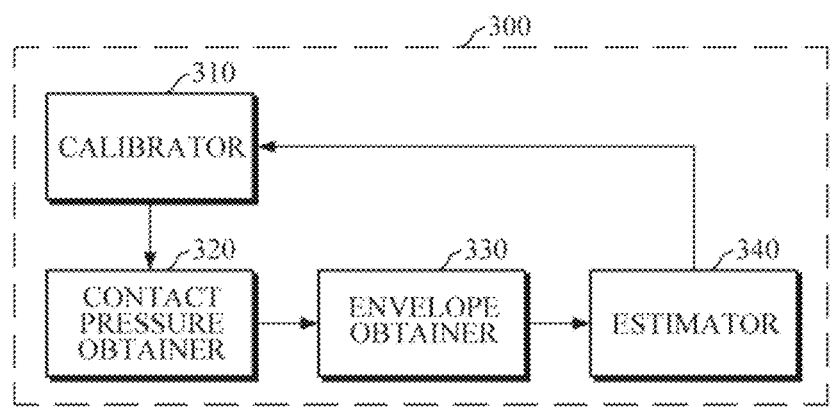
FIG. 3 is a block diagram illustrating an example of a processor of the apparatus for estimating bio-information according to the example embodiments of FIGS. 1 and 2.
Figure 4A:
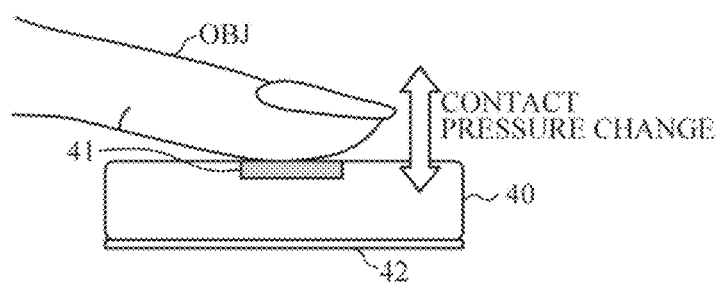

FIG. 3 is a block diagram illustrating an example of a processor 130 of the apparatus for estimating bio-information according to the example embodiments of FIGS. 1 and 2. FIGS. 4A and 4B are diagrams explaining a relationship between a change in contact pressure of an object and a contact area.

Referring to FIG. 3, the processor 300 according to an example embodiment of the present disclosure includes a calibrator 310, a contact pressure obtainer 320, an envelope obtainer 330, and a bio-information estimator 340.

Referring to FIG. 4A, an apparatus for estimating bio-information may include a main body 40, a PPG sensor 41 which is mounted on one surface of the main body 40 to come into contact with an object OBJ of a user, and a display module 42 which is mounted on the other side of the main body 40 to display a variety of information. A force sensor and a contact area sensor may be mounted in the main body 40. In this case, when a user contacts the pulse wave sensor 110 with an object and gradually increases contact pressure to estimate bio-information, the PPG sensor 41, the contact area sensor, and the contact force sensor may measure a PPG signal, a contact area, and a contact force respectively, as illustrated in FIG. 4B.

However, without need for a separate sensor for measuring a contact area of an object, the apparatuses 100 and 200 for estimating bio-information according to the example embodiments of the present disclosure may pre-obtain, as a reference contact area, a contact area at a specific time (e.g., a final contact area at a time when a maximum contact pressure is applied, or a contact area measured when an exerted contact pressure reaches a predetermined contact pressure) from an object as illustrated in FIG. 4B, and may estimate bio-information by using the reference contact area, such that accuracy in estimating bio-information may be improved, and the apparatuses may be manufactured in a small size.

The calibrator 310 may monitor occurrence of a calibration event, and in response to the occurrence of a calibration event, the calibrator 310 may obtain a reference contact area for the object of the user.

For example, the calibration event may be generated if there is no reference contact area for an object in the storage 220. For example, the calibration event may be generated at a time when a user uses the apparatuses 100 and 200 for estimating bio-information for the first time. Alternatively, the calibration event may be generated for various reasons, such as a change in object by a user at a time when the contact pressure obtainer 320 extracts a reference contact area from the storage 220 to obtain contact pressure, initialization of the apparatuses 100 and 200 for estimating bio-information, and the like.

In another example, the calibration event may be generated at predetermined calibration intervals. In particular, the calibration intervals may be preset based on a user's age, health condition, a change in measurement environment, and the like.

In yet another example, the calibration event may be generated based on a bio-information estimation result. Once the estimator 340 estimates bio-information, the calibrator 310 may determine whether to perform calibration by analyzing estimated bio-information values, contact forces, and/or contact pressure values which are estimated at previous times and stored in the storage 220, and estimated bio-information values, contact forces, and/or contact pressure values which are estimated at a current time. For example, if a variation in the estimated bio-information value at the current time compared to the estimated bio-information value at the previous time is greater than or equal to a predetermined threshold, or if a variation in the contact force at the current time compared to the contact force at the previous time is greater than or equal to a predetermined threshold, the calibrator 310 may determine that a reference contact area of an object is changed, or an object itself being in contact with the pulse wave sensor 110 is changed.

In still another example, the calibration event may be generated in response to a user's request. For example, if a user is in a situation where a frequently used object is not available, or if a user simply desires to change the object, the user may request calibration. However, the calibration event is not limited thereto.

In response to occurrence of the calibration event, the calibrator 310 may directly obtain a reference contact area of an object by using various modules (e.g., display module, touch screen, fingerprint sensor, image sensor, etc.) mounted in the apparatuses 100 and 200 for estimating bio-information, an area measurement application installed in the apparatuses 100 and 200, and the like; or the calibrator 310 may obtain a new reference contact area using various methods, such as receiving the reference contact area from an external device, receiving the reference contact area directly input by a user, and the like.

FIGS. 5A to 5E are diagrams illustrating various examples of obtaining a reference contact area. Various embodiments of obtaining a reference contact area will be described below with reference to FIGS. 5A to 5E, in which it is assumed that a user's object is a finger, but the example embodiments are not limited thereto.

Figure 5A:
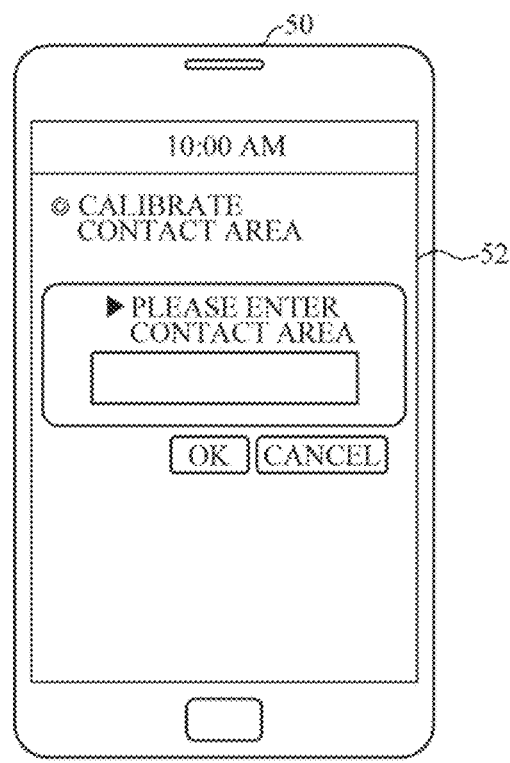
FIGS. 5A to 5E are diagrams illustrating various examples of obtaining a reference contact area.

Referring to FIG. 5A, the calibrator 310 may output an interface to a display module 52 mounted on a front surface of a main body 50 of the apparatuses 100 and 200 for estimating bio-information, so as to receive a reference contact area from an external device or a user which measures the reference contact area.

For example, a user may measure a reference contact area by using an external device (e.g., a smart device and the like). For example, when a user applies pressure to a surface of a display module of an external device, the external device may obtain a reference contact area by using a display module, a touch screen, a large-area fingerprint sensor, and/or an area measurement application, and the like.

Figure 5B:
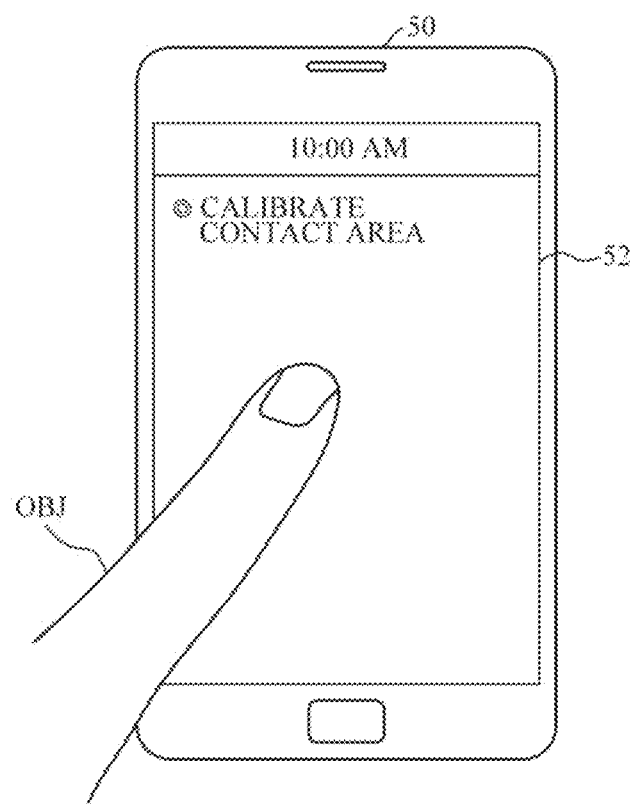
Figure 5C:
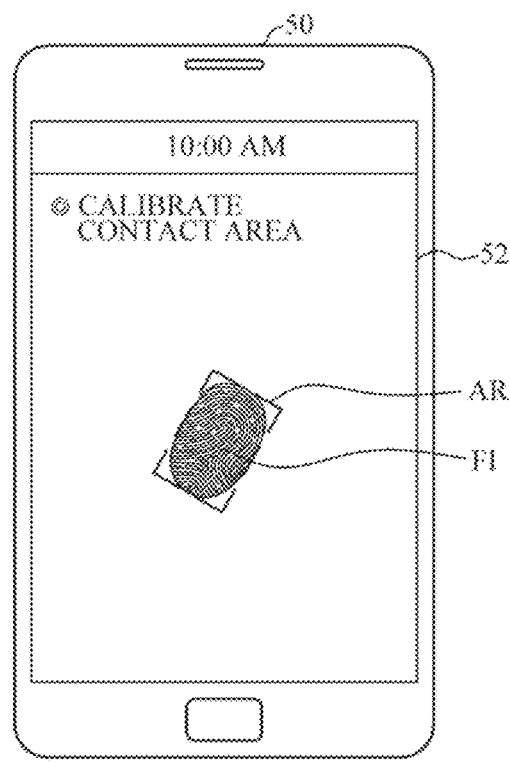
Figure 5D:
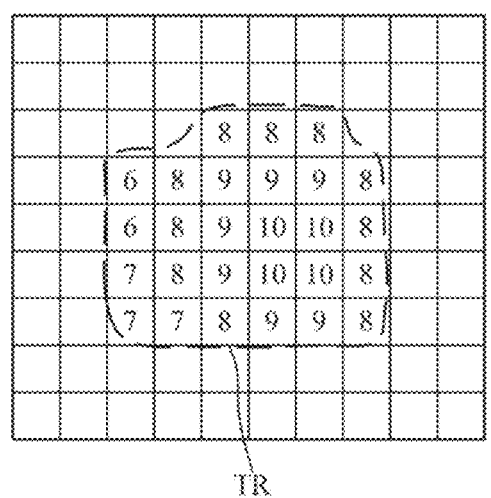
Figure 5E:
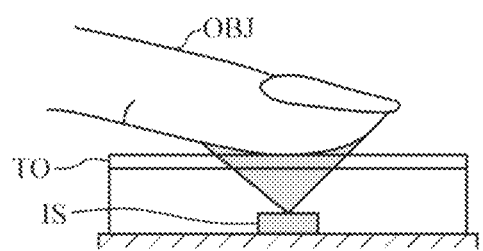

Alternatively, as illustrated in FIG. 5E, when a user presses a finger OBJ against a transparent object TO, such as a glass plate, and applies pressure thereto, the external device may obtain an image of the finger by using an image sensor IS, and may obtain a reference contact area by analyzing the finger image. For example, the external device may obtain a region of interest by analyzing the finger image at a time when the finger applies maximum pressure, and may obtain an area of the region of interest as a reference contact area. In this case, various known techniques may be used for image analysis, such that detailed description thereof will be omitted.

The user may obtain contact areas of the object a plurality of number of times by using the external device, and may use a statistics value (e.g., average value, median value, maximum value, minimum value, etc.) of the obtained contact areas as a reference contact area. In this case, an outlier may be excluded from the plurality of contact areas. The user may directly input the obtained reference contact area, obtained by using the external device, into the interface. Alternatively, by using the communication interface 230 to communicate with a communication module of the external device, the calibrator 310 may receive a reference contact area obtained by the external device, and may automatically input the received reference contact area into the interface.

In another example, a user may directly measure a fingerprint residual image, which remains after pressing a finger against a transparent object, such as a glass plate, and applying maximum pressure thereto, or a fingerprint made by pressing a finger onto an ink pad and rolling the finger onto paper and the like, and then may obtain a reference contact area based on a size of the measured fingerprint and may input the obtained reference contact area into the interface. In this case, in order to improve accuracy, a statistics value of the fingerprint sizes obtained by performing the above process a plurality of number of times, or a statistics value of the fingerprint sizes, from which an outlier is removed, may be input as a reference contact area.

Referring to FIGS. 5B and 5C, when a user contacts a display module 52, mounted on a main body 50 of the apparatuses 100 and 200 for estimating bio-information, with the finger OBJ and gradually increases pressure thereto, and then takes the finger OBJ off the display module 52 according to guide information, the calibrator 310 may obtain a reference contact area based on a residual fingerprint image FI remaining on a surface of the display module 52. For example, the calibrator 310 may execute an area measurement application installed in the apparatuses 100 and 200 for estimating bio-information, and may obtain a reference contact area based on a size AR of the residual fingerprint image which is measured by the area measurement application. The calibrator 310 may guide contact of the finger a plurality of number of times at predetermined time intervals, and may obtain a statistics value of the sizes of the residual fingerprint images which are measured a plurality of number of times.

Referring to FIG. 5D, the display module 52 of the apparatuses 100 and 200 for estimating bio-information may include a touch screen for receiving touch input. When a user places a finger on the display module 52 and applies pressure thereto, the calibrator 310 may obtain a reference contact area by using touch data generated by the touch screen. In this case, the touch data may show the magnitude of an amount of light received by each pixel of the touch screen.

For example, as illustrated in FIG. 5D, the calibrator 310 may extract a region, having an amount of light in each pixel of the touch screen which is greater than or equal to a threshold, as a region of interest TR, and may obtain an area of the extracted region of interest TR as a reference contact area. For example, the area of the region of interest TR may be obtained by multiplying a number of pixels included in the region of interest TR by a unit area of each pixel. In another example, based on a correlation between the intensity of pixels in the region of interest TR, i.e., a statistics value (e.g., sum total, maximum value, minimum value, average value, median value, a difference between the maximum value and the minimum value, etc.) of magnitudes of amounts of light, and a contact area, the calibrator 310 may obtain a reference contact area. That is, as a contact area increases with an increase in the contact pressure of a finger, the amount of light received by each pixel also increases, such that a correlation between the contact area and the amount of light in each pixel may be pre-defined by various linear/non-linear functions.

Referring to FIG. 5E, the apparatuses 100 and 200 for estimating bio-information may include an image sensor IS. The calibrator 310 may guide a user to acquire a contact image of a finger by using the image sensor IS. As described above, when a user applies pressure to a transparent object TO, such as a glass plate, while pressing the finger OBJ against the transparent object TO, the image sensor acquires an image of the finger, and the calibrator 310 may obtain a reference contact area by analyzing the finger image using an image analysis algorithm.

Furthermore, the display module 52 of the apparatuses 100 and 200 for estimating bio-information may include a large-area fingerprint sensor. Examples of the large-area fingerprint sensor may be an optical sensor, a capacitive sensor, or an ultrasonic sensor, but is not limited thereto. The large-area fingerprint sensor may have a larger surface area than a surface area of the pulse wave sensor 110, and may disposed separately from the pulse wave sensor 110. Since the processor 130 is enabled to estimate bio-information (e.g., blood pressure) by measuring a pulse wave signal and a contact area of the finger separately at different times, the large-area fingerprint sensor does not necessarily have to be integrated into the pulse wave sensor 110, or stacked with the pulse wave sensor 110. The large-area fingerprint sensor may be disposed anywhere in the display module 52 to provide the user with a large contact surface and thereby to enhance a measurement accuracy, without requiring additional space for the large-area fingerprint sensor. When the user contacts the display module 52 with the finger and applies pressure thereto, the calibrator 310 may obtain a reference contact area based on the fingerprint image of the finger which is acquired by the large-area fingerprint sensor.

Referring back to FIG. 3, upon receiving a contact force from the force sensor 120, the contact pressure obtainer 320 may obtain contact pressure based on the received contact force and the reference contact area obtained by the calibrator 310.

The envelope obtainer 330 may obtain an oscillometric envelope by using the pulse wave signal, measured by the pulse wave sensor 110, and the contact pressure obtained by the contact pressure obtainer 320.

Figure 6A:
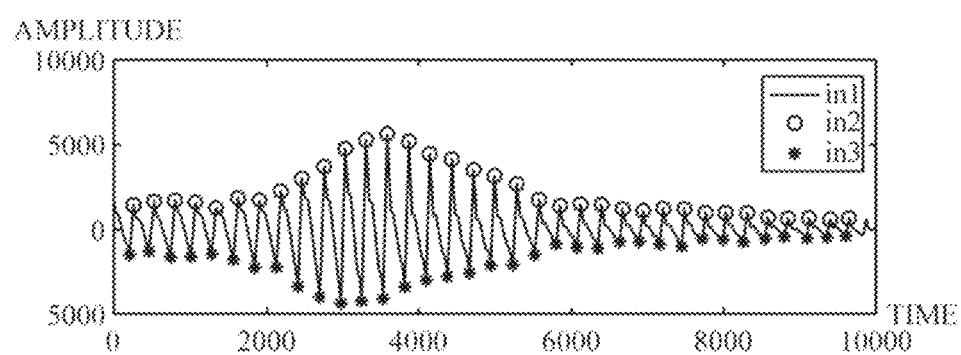
FIGS. 6A and 6B are diagrams explaining an example of estimating bio-information based on oscillometry.
Figure 6B:
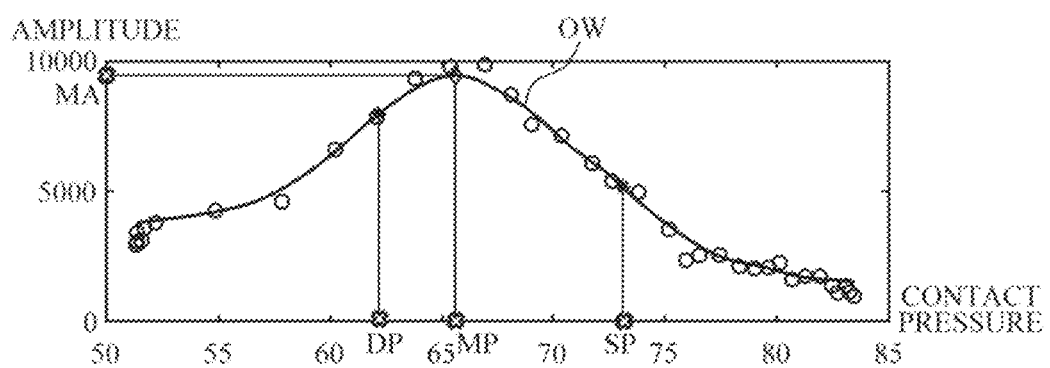

FIGS. 6A and 6B are diagrams explaining an example of estimating bio-information based on oscillometry.

For example, FIG. 6A illustrates a PPG signal measured by the pulse wave sensor 110 when a user gradually increases contact pressure while contacting the pulse wave sensor 110 with an object. As illustrated in FIG. 6A, when the user gradually increases pressure while the object of the user is in contact with the pulse wave sensor 110, the amplitude of the pulse wave signal also shows a gradually increasing trend during a predetermined period of time. The envelope obtainer 330 may extract a peak-to-peak point of the pulse wave signal waveform by subtracting a negative (−) amplitude value in3 from a positive (+) amplitude value in2 of a waveform envelope in1 at each measurement time, and may obtain the oscillometric envelope OW by plotting the peak-to-peak amplitude at each measurement time against the contact pressure value at the same point in time, as illustrated in FIG. 6B.

Referring to FIG. 6B, the estimator 340 may obtain features for estimating bio-information (e.g., blood pressure) from the obtained oscillometric envelope OW. The estimator 340 may obtain, as features, an amplitude value MA at a maximum peak point, a contact pressure value MP at the maximum peak point, contact pressure values SP and DP at the left and right points which are distant from the contact pressure value MP at the maximum peak point and which correspond to amplitude values having a preset peak ratio (e.g., 0.5 to 0.7) to the amplitude value MA at the maximum peak point, and the like from the oscillometric envelope OW. However, the features are not limited thereto, and the estimator 340 may obtain additional features, such as a maximum amplitude value, a time value corresponding to the maximum amplitude value, time and amplitude values at points related to a propagation wave and a reflection wave, a combination of the obtained values, and the like.

Upon extracting the features, the estimator 340 may estimate bio-information by applying a pre-defined bio-information estimation model. The bio-information estimation model may be defined as various linear or non-linear combination functions, such as addition, subtraction, division, multiplication, logarithmic value, regression equation, and the like, with no specific limitation. For example, the following Equation 1 represents a simple linear function.

$$y=ax+b \qquad \text{[Equation 1]}$$

Herein, y denotes an estimated bio-information value to be obtained; x denotes an extracted feature value; and a and b are values pre-obtained by preprocessing, and may be defined differently according to types of bio-information and user characteristics. For example, by using the above Equation 1 which is defined for each of mean arterial pressure, diastolic blood pressure, and systolic blood pressure, the estimator 340 may independently estimate each blood pressure. For example, by inputting the extracted feature values MP, DP, and SP into the function, which is defined for each of the feature values, the estimator 340 may obtain MAP, SBP, and DBP independently.

Figure 7:
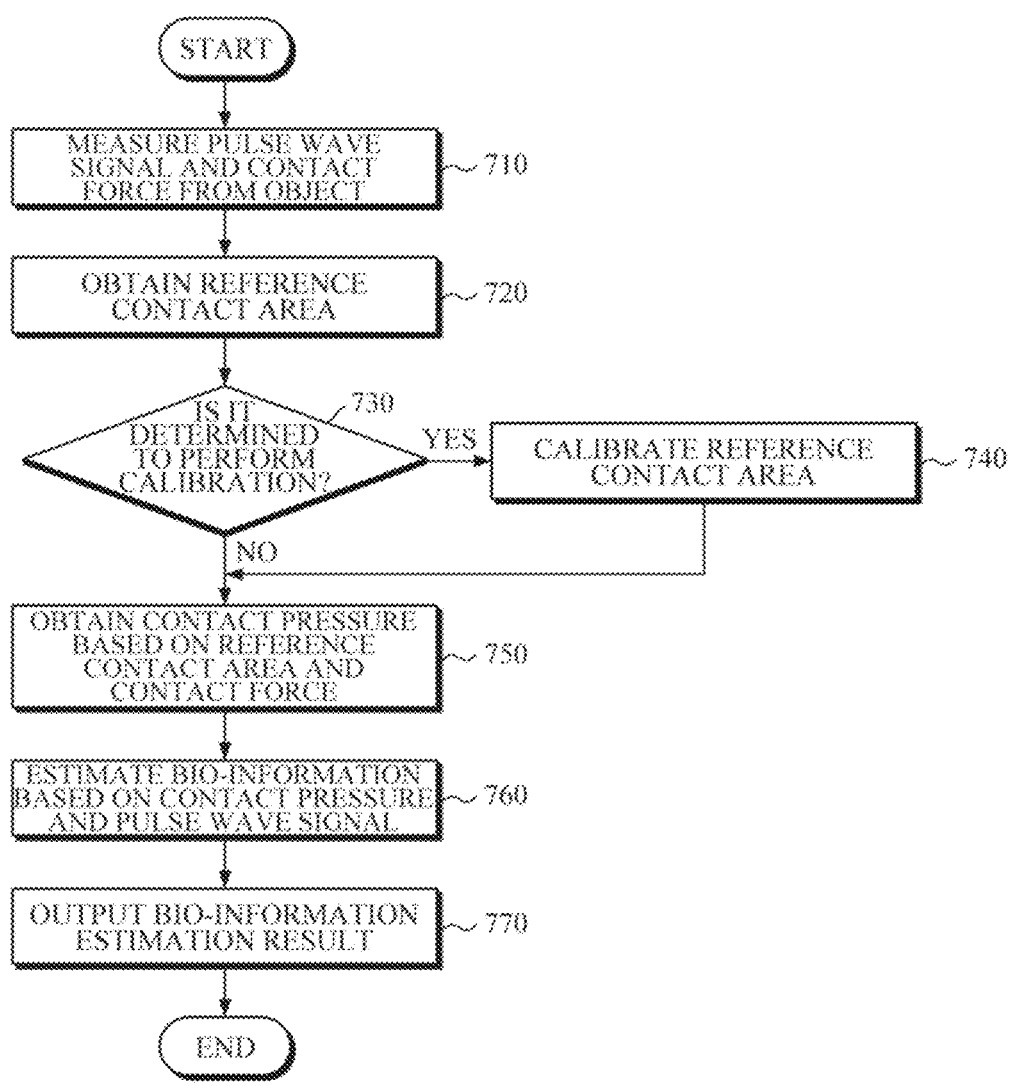
FIG. 7 is a flowchart illustrating a method of estimating bio-information according to an example embodiment of the present disclosure.

FIG. 7 is a flowchart illustrating a method of estimating bio-information according to an example embodiment of the present disclosure. The method of estimating bio-information of FIG. 7 may be an example of the method of estimating bio-information which is performed by the aforementioned apparatuses 100 and 200 for estimating bio-information, and a description thereof will be briefly made below.

Referring to FIG. 7, in response to a request for estimating bio-information, the apparatuses 100 and 200 for estimating bio-information may measure a pulse wave signal and a contact force in operation 710 from an object when a user contacts a pulse wave sensor with the object and changes the contact force for a predetermined period of time. Upon receiving the request for estimating bio-information which is input by the user or which is generated at predetermined intervals, the apparatuses 100 and 200 for estimating bio-information may guide a contact position, a contact force, and the like of the object to estimate bio-information.

Then, the apparatuses 100 and 200 for estimating bio-information may obtain a pre-registered reference contact area for the object which is in contact with the pulse wave sensor to measure a pulse wave signal in operation 720.

Subsequently, the apparatuses 100 and 200 for estimating bio-information may determine whether to perform calibration of the reference contact area in operation 730. For example, if there is no reference contact area in a storage, or a calibration time of the reference contact area stored in the storage has elapsed, the apparatuses 100 and 200 for estimating bio-information may determine to perform calibration.

Next, upon determining to perform calibration in operation 730, the apparatuses 100 and 200 for estimating bio-information may calibrate the reference contact area in operation 740. For example, the apparatuses 100 and 200 for estimating bio-information may guide a user to obtain a reference contact area by referring to criteria such as the configuration of the apparatuses 100 and 200, applications installed therein, and a predetermined basic method of obtaining the reference contact area, and the like. As described above, the apparatuses 100 and 200 for estimating bio-information may obtain the reference contact area by using a display module of the apparatuses 100 and 200, a touch screen of the display module, an area measurement application, an image sensor, and an external device, or by direct measurement by a user. In this case, if the reference contact area may be obtained using a plurality of methods, a basic method may be predetermined and may be changed according to a user's setting.

However, at the time of estimating bio-information, the determining whether to perform calibration in operation 730 and the performing of calibration in operation 740 may be omitted.

Then, if it is determined that calibration is not required in 730, or if calibration is performed in 740, the apparatuses 100 and 200 for estimating bio-information may obtain contact pressure based on the obtained reference contact area and the contact force in 750.

Subsequently, the apparatuses 100 and 200 for estimating bio-information may estimate bio-information based on the contact pressure and the pulse wave signal in operation 760. For example, the apparatuses 100 and 200 for estimating bio-information may obtain an oscillometric envelope, which represents an amplitude of the pulse wave signal versus contact pressure, and may extract features for estimating bio-information by using the oscillometric envelope. For example, the apparatuses 100 and 200 for estimating bio-information may obtain, as features, a contact pressure value corresponding to a maximum amplitude, contact pressure values at the right and left points which correspond to amplitude values having a preset peak ratio to the maximum amplitude, and the like from the oscillometric envelope. Further, the apparatuses 100 and 200 for estimating bio-information may estimate bio-information by using a predefined bio-information estimation model.

Next, the apparatuses 100 and 200 for estimating bio-information may output a bio-information estimation result in 770. The apparatuses 100 and 200 for estimating bio-information may output a bio-information estimation result, a bio-information estimation history, warning information, and the like, by visual/non-visual methods using various output devices such as a display module, a speaker module, a haptic module, and the like.

FIGS. 8A to 8D are flowcharts illustrating various examples of calibrating a reference contact area in operation 740.

Figure 8A:
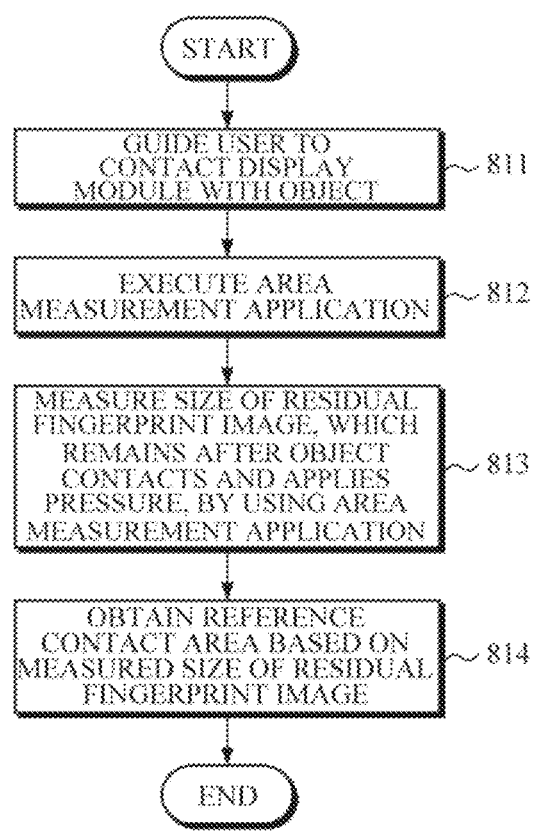
FIGS. 8A to 8D are flowcharts illustrating various examples of calibrating a reference contact area.

Referring to FIG. 8A, the apparatuses 100 and 200 for estimating bio-information may guide a user to contact a display module with an object in operation 811. For example, the apparatuses 100 and 200 for estimating bio-information may output a mark (circle, square, oval, arrow, etc.), which indicates a contact position, to the display module. In addition, the apparatuses 100 and 200 for estimating bio-information may visually output contact pressure to be applied by the object to the display module in the form of graphs and the like.

Then, the apparatuses 100 and 200 for estimating bio-information may execute an area measurement application in operation 812, and may measure a size of a residual fingerprint image, which remains after the object contacts and applies pressure, by using the area measurement application in operation 813. In this case, when the area measurement application automatically determines an outline of the residual fingerprint image, or a user manually determines an outline of the residual fingerprint image to be measured or corrects an outline which is determined automatically by the area measurement application, the area measurement application may calculate an area of the determined outline. The operation 813 may be performed a predetermined number of times.

Subsequently, the apparatuses 100 and 200 for estimating bio-information may obtain a reference contact area based on the size of the residual fingerprint image which is measured by the area measurement application in operation 814. For example, the apparatuses 100 and 200 for estimating bio-information may obtain the size of the residual fingerprint image directly as the reference contact area, and may obtain a value, obtained by adjusting the measured size of the residual fingerprint image according to predetermined criteria, as the reference contact area. Alternatively, upon obtaining a plurality of sizes of residual fingerprint images by performing the operation 813 a plurality of number of times, the apparatuses 100 and 200 for estimating bio-information may obtain a statistics value of the obtained sizes of the residual fingerprint images as the reference contact area.

Figure 8B:
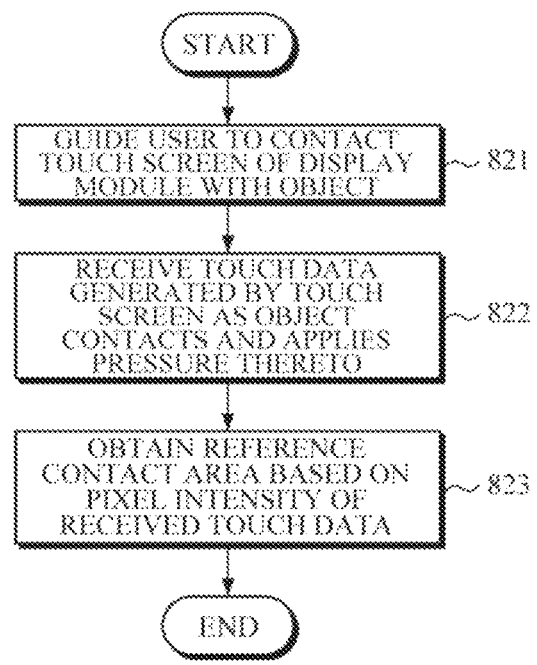

Referring to FIG. 8B, the apparatuses 100 and 200 for estimating bio-information may guide a user to contact a touch screen of the display module with an object in operation 821.

Then, the apparatuses 100 and 200 for estimating bio-information may receive touch data in operation 822, which are generated by the touch screen as the object contacts and applies pressure thereto, and may obtain a reference contact area based on a pixel intensity of the received touch data in operation 823. For example, the apparatuses 100 and 200 for estimating bio-information may obtain a region of interest based on the intensity of each pixel of the touch data obtained at a time when maximum pressure is applied by the object while gradually increasing pressure during a predetermined period of time, and may obtain an area of the region of interest, which is obtained by various methods as described above, as the reference contact area.

Figure 8C:
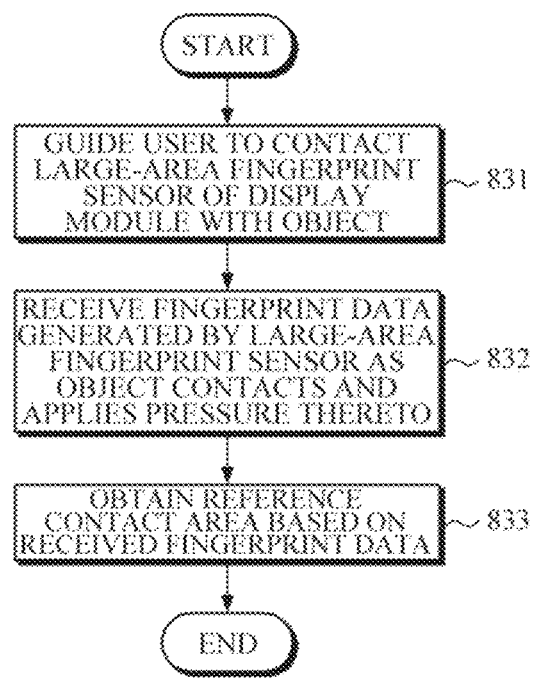

Referring to FIG. 8C, the apparatuses 100 and 200 for estimating bio-information may guide a user to contact a display module with an object in operation 831. In this case, the display module may include a large-area fingerprint sensor.

Then, the apparatuses 100 and 200 for estimating bio-information may receive fingerprint data in operation 832, which show fingerprint images generated by a large-area fingerprint sensor as the object contacts and applies pressure thereto, and may obtain the area of the fingerprint as the reference contact area based on the received fingerprint data in operation 833.

Figure 8D:
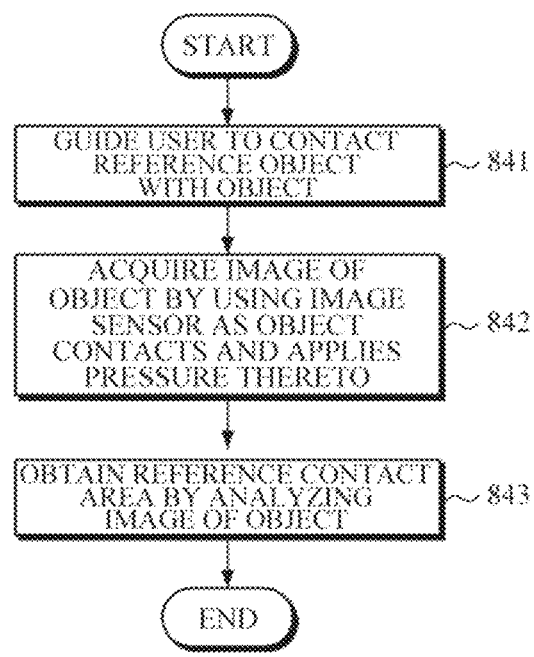

Referring to FIG. 8D, the apparatuses 100 and 200 for estimating bio-information may guide a user to contact an external reference object with an object of the user in operation 841. In this case, the reference object may be a hard, transparent object such as a glass plate.

Then, the apparatuses 100 and 200 for estimating bio-information may acquire an image of the object by using an image sensor in operation 842 as the object contacts and applies pressure thereto, and may obtain a reference contact area by analyzing the obtained image of the object in operation 843.

Figure 9:
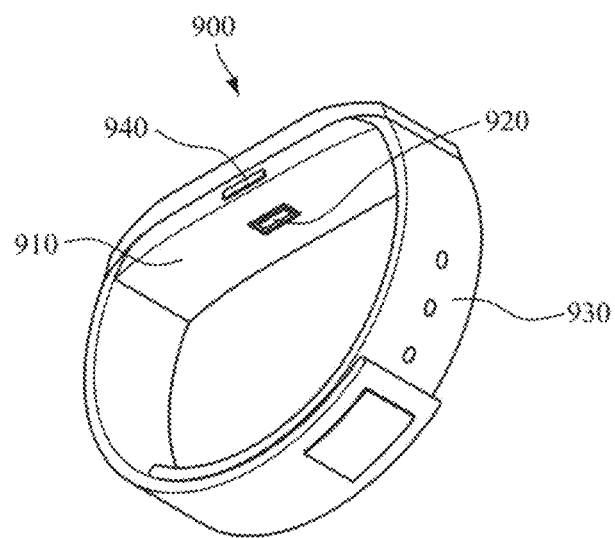
FIG. 9 is a diagram illustrating an example of a wearable device, to which the apparatus for estimating bio-information is applied.

FIG. 9 is a diagram illustrating an example of a wearable device, to which the aforementioned example embodiments of the apparatuses 100 and 200 for estimating bio-information are applied.

Referring to FIG. 9, the wearable device 900 includes a main body 910 and a strap 930.

The strap 930 may be flexible, and may be connected to both ends of the main body 910 to be bent around a user's wrist or may be bent in a manner Which allows the strap 930 to be detached from a user's wrist. Alternatively, the strap 930 may be formed as a band that is not detachable. In this case, air may be injected into the strap 930 or an airbag may be included in the strap 930, so that the strap 930 may have elasticity according to a change in pressure applied to the wrist, and the change in pressure of the wrist may be transmitted to the main body 910.

A batters, which supplies power to the wearable device 900, may be embedded in the main body 910 or the strap 930.

Further, a sensor part 920 is mounted on one side of the main body 910. The sensor part 920 may include a pulse wave sensor 110 which measures a pulse wave signal from blood vessel tissue of the wrist being in contact with an area sensor; and a force sensor 120 which measures a contact force between the wrist and the pulse wave sensor 110. The pulse wave sensor 110 may include one or more light sources 110a for emitting light onto the wrist; and a detector 110b for detecting light reflected or scattered from the skin of the wrist and the blood vessel tissue. In this case, each of the light sources 110a may emit light of different wavelengths, and may be disposed at different distances from the detector 110b.

When a user changes contact pressure between the wrist and the sensor part 920 for a predetermined period of time for estimating bio-information, the sensor part 920 may measure the pulse wave signal and the contact force. In this case, the user may change contact pressure between the wrist and the sensor part 920 by pressing a display, mounted on one surface of the main body 910, e.g., a surface opposite to the sensor part 920, a finger of the other hand with a gradually increasing force while wearing the main body 910. Alternatively, the user may change a thickness of the wrist by making hand movements, e.g., slowly opening the hand after clenching a first while wearing the main body 910 on the wrist. In this case, the change in the thickness of the wrist leads to a change in tension of the strap wrapped around the wrist, thereby causing a change in contact pressure between the wrist and the sensor part 920.

In addition, the main body 910 may include a processor, which may estimate bio-information by using the pulse wave signal and the contact force, and may control various other functions of the wearable device 900.

The processor may be electrically connected to the sensor part 920, and may control the sensor part 920 in response to a user's request for estimating bio-information. The processor may estimate bio-information based on the pulse wave signal and the contact force which are received from the sensor part 920. For example, the processor may obtain a reference contact area for the wrist which is pre-stored in a storage, and may obtain contact pressure by using the reference contact area and the contact force. Further the processor may obtain an oscillometric envelope by using the contact pressure and an amplitude of the pulse wave signal, and may estimate bio-information based on the obtained oscillometric envelope.

Upon receiving the request for estimating bio-information from a user, the processor may guide contact pressure for the user through a display, so that the user may change contact pressure between the sensor part 920 and the object by applying pressure to the main body 910.

In this case, the display may be mounted on a front surface of the main body 910, and may visually output guide information on contact pressure and/or an estimation result of bio-information. In this case, the display may be a display module including a touch screen and/or a large-scale fingerprint sensor, and the like, and the processor may obtain a reference contact area for the wrist by using the display module of the display.

A storage may be mounted in the main body 910, and may store a variety of information processed by the processor, and reference information such as a reference contact area for estimating bio-information and the like.

Further, the wearable device 900 may include a manipulator 940 which receives a control command of a user and transmits the received control command to the processor. The manipulator 940 may be mounted on a side surface of the main body 910, and may include a function for inputting a command for power on/off of the wearable device 900.

Moreover, the wearable device 900 may include a communication interface for transmitting and receiving various data to and from an external device, and various other modules for performing additional functions provided by the wearable device 900. In response to a request of the processor, the communication interface may transmit a request for a reference contact area to an external device, e.g., a user's smartphone; and once the external device obtains the reference contact area from the user, the communication interface may receive the obtained reference contact area from the external device.

Figure 10:
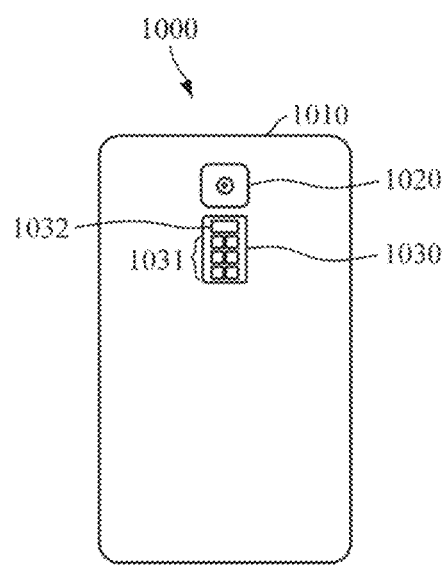
FIG. 10 is a diagram illustrating an example of a smart device, to which the apparatus for estimating bio-information is applied.

FIG. 10 is a diagram illustrating a smart device, to which the example embodiments of the apparatus for estimating bio-information are applied. In this case, the smart device may be a smartphone, a tablet PC, and the like.

Referring to FIG. 10, the smart device 1000 includes a main body 1010 and a sensor part 1030 mounted on one surface of the main body 1010. The sensor part 1030 may include a pulse wave sensor, including one or more light sources 1031 and a detector 1032, and a force sensor. As illustrated in FIG. 10, the sensor part 1030 may be mounted on a rear surface of the main body 1010, but is not limited thereto, and may be configured in combination with a fingerprint sensor or a touch panel formed on the front surface of the main body 1010. In this case, the fingerprint sensor or the touch panel may perform a function of an area sensor, and the pulse wave sensor and the force sensor may be mounted below the fingerprint sensor or the touch panel.

In addition, a display may be mounted on a front surface of the main body 1010. The display may visually display a bio-information estimation result and the like. The display may be a display panel including a touch screen and/or a large-area fingerprint sensor, and the like, and may transmit a variety of information, input through the touch screen and/or the large-area fingerprint sensor, and the like, to the processor.

Moreover, an image sensor 1020 may be mounted in the main body 1010. When a user's finger approaches the sensor part 1030 to measure a pulse wave signal, the image sensor 1020 may capture an image of the finger and may transmit the captured image to the processor.

In this case, based on the image of the finger, the processor may identify a relative position of the finger with respect to an actual position of the sensor part 1030, and may provide the relative position of the finger to the user through the display, so that pulse wave signals may be measured with improved accuracy. Further, the processor may determine a type of the finger, which is in contact with the pulse wave sensor, based on the finger image measured by the image sensor.

Once the sensor part 1030 measures the pulse wave signal and the contact force, the processor may obtain a reference contact area of the finger, which is in contact with the pulse wave sensor, from the storage, and may estimate bio-information by using the contact force, the reference contact area, and the pulse wave signal. In this case, the processor may determine a type of the finger (e.g., index finger of the right hand), which is in contact with the pulse wave sensor, based on the finger image acquired by the image sensor, and may obtain a reference contact area corresponding to the determined type of the finger.

As described above, the processor may calibrate the reference contact area of the finger by using the display, and may store the obtained reference contact area in the storage. The processor may perform various other example embodiments of the aforementioned apparatus for estimating bio-information, and a detailed description thereof will be omitted.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
    a touch screen configured to generate touch data when the touch screen is touched by an object;
    a photoplethysmography (PPG) sensor configured to measure a PPG signal from the object during a bio-information measurement;
    a force sensor configured to measure a force exerted by the object to the PPG sensor during the bio-information measurement;
    a processor configured to:
        during calibration, obtain a reference contact area between the object and the touch screen, based on the touch data that is generated by the touch screen to represent a light intensity of each of a plurality of pixels of the touch screen, by determining one or more pixels that have the light intensity greater than a threshold value as the reference contact area, among the plurality of pixels;
        during the bio-information measurement, obtain a contact pressure based on the force that is obtained during the bio-information measurement, and the reference contact area between the object and the touch screen that is obtained during the calibration and stored in the apparatus; and
        estimate the bio-information based on the contact pressure and the PPG signal; and
    a storage configured to store the reference contact area,
    wherein the processor is further configured to, when the PPG signal is measured, retrieve the reference contact area from the storage.

2. The apparatus of claim 1, wherein the PPG sensor comprises:
    a light source configured to emit a light onto the object; and
    a detector configured to detect the light reflected or scattered from the object.

3. The apparatus of claim 1, wherein the processor is further configured to determine whether to perform the calibration based on at least one of a determination of whether the storage stores the reference contact area, a user's request, a predetermined calibration interval, and bio-information estimation history.

4. The apparatus of claim 1, wherein the processor is further configured to, during the calibration, obtain the reference contact area based on a residual fingerprint image which remains on the touch screen after the user contacts the touch screen with the object.

5. The apparatus of claim 4, wherein the processor is further configured to, during the calibration, execute an area measurement application to measure a size of the residual fingerprint image, and obtain the size of the residual fingerprint image as the reference contact area.

6. The apparatus of claim 1, wherein the touch screen comprises a fingerprint sensor that provides a contact surface which has a larger surface area than a surface area of the PPG sensor, and disposed separately from the PPG sensor.

7. The apparatus of claim 1, wherein the PPG sensor and the force sensor are configured to operate at a same time in parallel to measure the PPG signal and the force, in a same time line, and
    wherein the processor is further configured to identify a maximum contact area as the reference contact area, among continuously increasing contact areas that are measured during the calibration.

8. The apparatus of claim 1, wherein the processor is further configured to obtain an oscillometric envelope which represents an amplitude of the PPG signal versus the contact pressure, and estimate the bio-information based on the oscillometric envelope.

9. The apparatus of claim 1, wherein upon receiving a request for estimating the bio-information, the processor is further configured to provide information indicating at least one of a contact position of the object and a contact force to be exerted by the object to the PPG sensor.

10. The apparatus of claim 1, wherein the bio-information comprises one or more of blood pressure, vascular age, arterial stiffness, aortic pressure waveform, vascular compliance, stress index, and degree of fatigue.

11. A method of estimating bio-information, the method comprising:
    during a bio-information measurement, measuring a photoplethysmography (PPG) signal from an object;
    during the bio-information measurement, measuring a force exerted by the object;
    during calibration, obtain a reference contact area between the object and a touch screen, based on touch data that is generated when the touch screen is touched to represent a light intensity of each of a plurality of pixels of the touch screen, by determining one or more pixels that have the light intensity greater than a threshold value as the reference contact area, among the plurality of pixels;

obtaining a contact pressure based on the force that is obtained during the bio-information measurement, and the reference contact area between the object and the touch screen that is obtained during the calibration;

estimating bio-information based on the contact pressure and the PPG signal;

storing, in a storage, the reference contact area; and retrieving the reference contact area from the storage when the PPG signal is measured.

12. The method of claim 11, further comprising, in response to determining that no reference contact area is stored for the object, or in response to determining that the calibration of the reference contact area is required, performing the calibration for obtaining the reference contact area.

13. The method of claim 11, wherein the obtaining the reference contact area comprises, obtaining the reference contact area based on a residual fingerprint image which remains on the touch screen after a user contacts the touch screen with the object.

14. The method of claim 13, wherein the obtaining the reference contact area comprises:

The method of claim 13, wherein the obtaining the executing an area measurement application to measure a size of the residual fingerprint image; and obtaining the size of the residual fingerprint image as the reference contact area.

15. The method of claim 11, wherein the obtaining the reference contact area comprises, when the user contacts the touch screen with the object, obtaining the reference contact area based on fingerprint data generated by a fingerprint sensor of the touch screen.

16. The method of claim 11, wherein the obtaining the reference contact area comprises:

identifying a maximum contact area as the reference contact area, among continuously increasing contact areas that are measured during the calibration.

17. The method of claim 11, wherein the estimating the bio-information comprises obtaining an oscillometric envelope which represents an amplitude of the PPG signal versus the contact pressure, and estimating the bio-information based on the oscillometric envelope.

* * * * *